US010106768B2

(12) United States Patent
Kim et al.

(10) Patent No.: US 10,106,768 B2
(45) Date of Patent: Oct. 23, 2018

(54) MICRO CELL CULTURING DEVICE

(71) Applicant: UNIST ACADEMY-INDUSTRY RESEARCH CORPORATION, Ulsan (KR)

(72) Inventors: Tae Sung Kim, Ulsan (KR); Min Seok Kim, Gwangju (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 196 days.

(21) Appl. No.: 14/908,124

(22) PCT Filed: May 20, 2014

(86) PCT No.: PCT/KR2014/004483
§ 371 (c)(1),
(2) Date: Jan. 28, 2016

(87) PCT Pub. No.: WO2015/016471
PCT Pub. Date: Feb. 5, 2015

(65) Prior Publication Data
US 2016/0208210 A1 Jul. 21, 2016

(30) Foreign Application Priority Data
Jul. 29, 2013 (KR) ...................... 10-20103-0089699

(51) Int. Cl.
C12M 1/34 (2006.01)
C12M 1/32 (2006.01)
C12M 3/06 (2006.01)

(52) U.S. Cl.
CPC ............ *C12M 41/40* (2013.01); *C12M 23/12* (2013.01); *C12M 23/16* (2013.01)

(58) Field of Classification Search
CPC ....... C12M 41/40; C12M 23/12; C12M 23/16
See application file for complete search history.

(56) References Cited

U.S. PATENT DOCUMENTS

2006/0003436 A1* 1/2006 DiMilla ................ C12M 29/10
435/284.1
2006/0216819 A1 9/2006 Yasuda et al.
2010/0311158 A1 12/2010 Kang et al.

FOREIGN PATENT DOCUMENTS

JP 2006-010656 A 1/2006
KR 10-2006-0009262 A 1/2006
(Continued)

OTHER PUBLICATIONS

International Search Report for PCT/KR2014/004483 dated Sep. 29, 2014 from Korean Intellectual Property Office.

*Primary Examiner* — Michael L Hobbs
(74) *Attorney, Agent, or Firm* — Revolution IP, PLLC

(57) ABSTRACT

A micro cell culturing device including: a substrate; an elastomer seated and arranged on an upper surface of the substrate; a test chamber indented to a lower surface of the elastomer at a predetermined height, the lower surface of the elastomer facing the upper surface of the substrate; a main channel indented to the lower surface of the elastomer at a predetermined height, the main channel being spaced apart from the test chamber; a connection channel indented to the lower surface of the elastomer and arranged between the test chamber and the main channel to connect the test chamber and the main channel; and a pressure adjusting unit for pressurizing the elastomer. A height of the connection channel is lower than heights of the test chamber and the main channel.

5 Claims, 4 Drawing Sheets

(56) References Cited

FOREIGN PATENT DOCUMENTS

| KR | 10-2010-0131623 A | 12/2010 |
|----|-------------------|---------|
| KR | 10-1287690 B1 | 7/2013 |
| WO | 2009/126524 A2 | 10/2009 |

\* cited by examiner

MICRO CELL CULTURING DEVICE

CROSS REFERENCE TO PRIOR APPLICATIONS

This application is a National Stage Application of PCT International Patent Application No. PCT/KR2014/004483 filed on May 20, 2014, under 35 U.S.C. § 371, which claims priority to Korean Patent Application No. 10-2013-0089699 filed on Jul. 29, 2013, which are all hereby incorporated by reference in their entirety.

TECHNICAL FIELD

The present invention relate to a micro cell culturing device.

BACKGROUND ART

In general, cell migration refers to movement of a living organism or individual cells due to various physical, chemical or biological stimulus, and is deeply related to various diseases and biological phenomena in human body such as infection of AIDS, germs, bacteria or the like, arteriosclerosis, arthritis, periodontitis, psoriasis, cancer, multiple sclerosis, male sterility, asbestos poisoning, or ozone poisoning.

However, an evaluation assay for cell migration according to the conventional art is mostly directed to two-dimensional cell migration, and only crawling of cells can be observed by using the conventional evaluation assay. However, cells actually exist three-dimensionally in reality, and thus in many cases, results that are different from actual phenomena are acquired from the conventional evaluation assay.

Assays for analyzing three-dimensional cell migration, histogenesis, form changes, or cell differentiation or the like have been developed overseas, but the assays still have limitations in exposing cells under particular conditions or copying actual three-dimensional migration occurring inside a living organism. Moreover, it is difficult to effectively evaluate and quantify an experimental result. When introducing a scaffold formed of an extracellular matrix (ECM) between microfluidic channels, advantages of microfluidic technology may be maintained, and at the same time, cell reaction may be mimicked three-dimensionally under an evaluation environment for evaluating, for example, cell migration and form changes, histogenesis, or cell differentiation. The above-described advantages are disclosed in International Patent Application No. WO2009/126524. This related art succeeded in mimicking formation of new blood vessels in 3D by introducing a collagen scaffold, which is one kind of ECM, between microfluidic channels. Also, the related art also discloses results of research on reaction between an endothelial cell of a blood vessel and a cancer cell, reaction between a liver cell and an endothelial cell of a blood vessel, and reaction of nerve cells.

Microfluidic technology may provide a micro environment around cells, and allows real-time observation of the cells and accurate quantification of reaction of the cells, reduction in the amount of cells or samples used, and evaluation of various experimental conditions. In addition, a technique of integrating a scaffold may induce a cell three-dimensionally, and allows for cultivation of cells according to various directions, for example, inwardly into the scaffold or on two sides of the scaffold. Thus, culturing of diverse cells at a time is enabled, and this allows research of an interaction between cells and research of an interaction between a cell and the scaffold itself, and the cells cultivated in the above-described manner may also be used in developing a medical material. Moreover, the effect of various materials such as nano-materials, medication, or protein, on a cell may be evaluated three-dimensionally.

However, a microfluidic platform according to the related art requires a pillar array having several tens to hundreds; a to fix space between a scaffold and a channel. If a pillar is not present, a scaffold may leak through a channel, and thus may not be used. For reference, a scaffold is mostly in the form of liquid and is hardened after being injected to a particular position in a channel, and a pillar is needed to confine the injected scaffold at a particular position before the scaffold is hardened.

However, the microfluidic platform described above has limited area for reaction of cells due to the pillar that prevents leakage of the scaffold, and mass production of the microfluidic platform is difficult. Also, the pillar is continuously seen during an observation process and thus disturbs quantification, and moreover, the main problem lies in that cells first react with the pillar rather than with the scaffold.

DETAILED DESCRIPTION OF THE INVENTION

Technical Problem

The present invention provides a micro cell culturing device cultivating cells easily by partitioning microchambers and then adjusting a culturing environment, without having to use a scaffold channel.

Technical Solution

According to an aspect of the present invention, there is provided a micro cell culturing device including: a substrate; an elastomer seated and arranged on an upper surface of the substrate; a test chamber indented to a lower surface of the elastomer at a predetermined height, wherein the lower surface of the elastomer faces the upper surface of the substrate, and cells flow in the test chamber; a main channel indented to the lower surface of the elastomer at a predetermined height, wherein the main channel is spaced apart from the test chamber, and cells flow in the main channel; a connection channel indented to the lower surface of the elastomer at a predetermined height and arranged between the test chamber and the main channel to connect the test chamber and the main channel to each other; and a pressure adjusting unit for pressurizing the elastomer, wherein a height of the connection channel is lower than heights of the test chamber and the main channel, and when the pressure adjusting unit pressurizes the elastomer, the connection channel is maintained at such a height that migration of the cells in the test chamber to the main channel is prevented.

The connection channel and the test chamber may have a height ratio of 1:10 to 1:100.

The connection channel and the main channel may have the same height.

The connection channel may have a height of 50 nm to 500 nm due to the elastomer being pressurized by the pressure adjusting unit.

The elastomer may be PDMS.

The pressure adjusting unit may include: a pressurizing plate having a plate shape and arranged on the elastomer; and an adjustment screw having two ends in a length direction that are respectively screw-coupled to the pressurizing plate and the substrate to connect the pressurizing plate and the substrate to each other.

Effect of the Invention

According to the micro cell culturing device of the present invention, an elastomer, into which a test chamber, a main channel, and a connection channel are indented at a predetermined height, is seated and arranged on a substrate, wherein the connection channel is formed to have a lower height than the test chamber and the main channel, and the elastomer is pressurized and compressed by using a pressure adjusting unit. Thus, the connection channel allows a fluid injected into the main channel to diffuse into the test chamber but prevents migration of cells in the test chamber to the main channel, thereby performing stable culturing while the cells are maintained inside the test chamber.

BRIEF DESCRIPTION OF THE DRAWINGS

These and/or other aspects will become apparent and more readily appreciated from the following description of the embodiments, taken in conjunction with the accompanying drawings in which.

BEST MODE

Hereinafter, preferred embodiments of the present invention will now be described with reference to the attached drawings.

Figure 1:
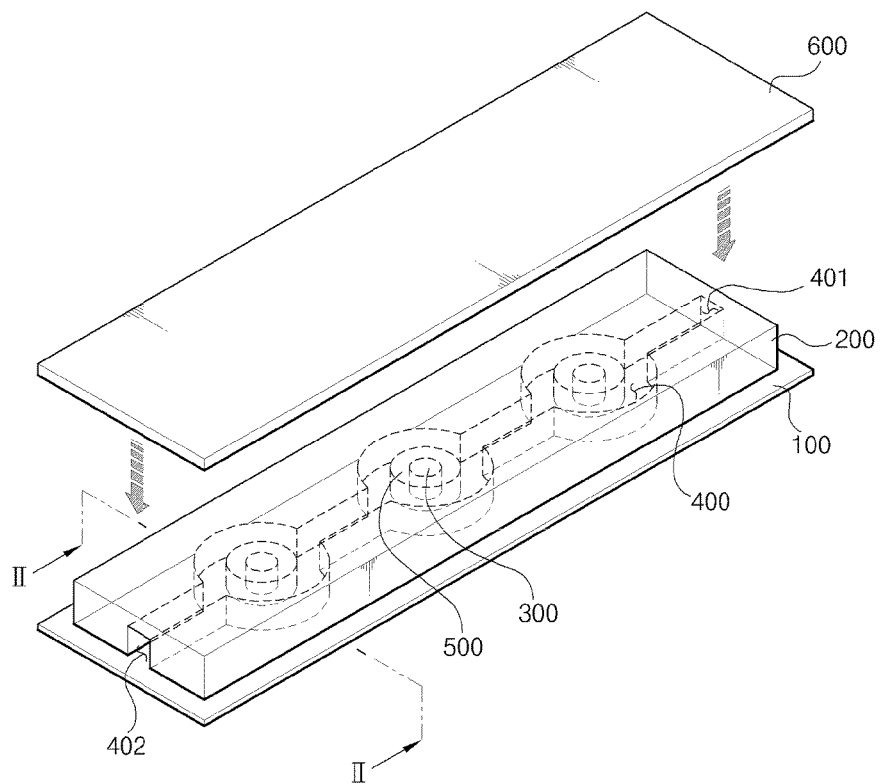
FIG. 1 is a perspective view of a micro cell culturing device according to an embodiment of the present invention.
Figure 2:
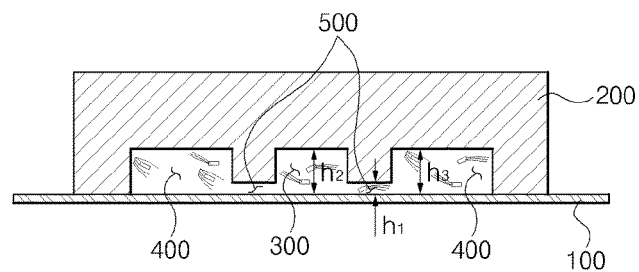
FIG. 2 is a cross-sectional view of the micro cell culturing device cut along a line II-II of FIG. 1.
Figure 3:
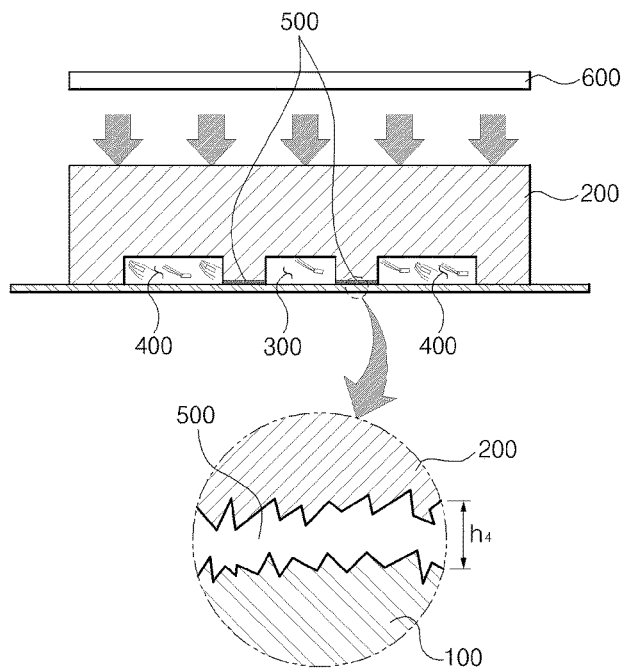
FIG. 3 is a cross-sectional view of the micro cell culturing device of FIG. 2 in a pressurized state.

FIG. 1 is a perspective view of a micro cell culturing device according to an embodiment of the present invention. FIG. 2 is a cross-sectional view of the micro cell culturing device cut along a line II-II of FIG. 1. FIG. 3 is a cross-sectional view of the micro cell culturing device of FIG. 2 in a pressurized state. The micro cell culturing device includes a substrate 100, an elastomer 200, a test chamber 300, a main channel 400, a connection channel 500, and a pressure adjusting unit 600.

The substrate 100 is to which a fluid is moved and where cells are cultivated via the elastomer 200, which will be described later. The substrate 100 may be formed of a transparent glass, but is not limited thereto, and may also be formed of a plastic or a synthetic resin material that is optically transparent.

It is advantageous when a surface of the substrate 100 is hydrophilic, and when an angle of contact of a fluid to be injected is equal to or less than 90 degrees, the fluid may be spontaneously injected into the test chamber 300 and the main channel 400, which will be described later, without an additionally peripheral device such as a pump. If a surface of the substrate 100 is hydrophobic or an angle of contact of a fluid to be injected is equal to or greater than 90 degrees, a peripheral device for injecting the fluid, such as a pump, may be additionally included.

The elastomer 200 is seated and arranged on an upper surface of the substrate 100, and allows the test chamber 300, the main channel 400, and the connection channel 500, which will be described later, to be formed on the substrate 100. The elastomer 200 is pressurized and compressed by using the pressure adjusting unit 600, which will be described later, and is formed of an elastic material that returns to its original state after a pressurizing force via the pressure adjusting unit 600 is removed later. In other words, the elastomer 200 may be preferably polydimethylsiloxane (PDMS), but is not limited thereto, and a polymer material such as polymethylmethacrylate (PMMA), polyacrylates, polycarbonates, polycyclic olefins, polyimides, or polyurethanes may also be selectively used as the elastomer 200.

The test chamber 300 is a flow path portion into which cells are introduced. The test chamber 300 is indented, at a predetermined height, to a lower central portion of the elastomer 200 facing the upper surface of the substrate 100 so that the test chamber 300 is formed along an upper central portion of the substrate 100. Cells are injected into the test chamber 300 through the main channel 400 which will be described later. It is obvious that an inlet (not shown), through which the cells are directly injected into the test chamber 300, and an outlet (not shown) that immediately discharges the cells in the test chamber 300 out of the test chamber 300 may be respectively connected to two ends of the test chamber 300.

The main channel 400 is a flow path portion in which a fluid flows. That is, various fluids for cultivating cells are injected into the main channel 400. The main channel 400 is indented, at a predetermined height, to the lower surface of the elastomer 200 facing the upper surface of the substrate 100 such that the main channel 400 is spaced apart from the test chamber 300 by a predetermined distance. Here, while a pair of main channels 400 are illustrated in FIG. 1 as being indented to the lower surface of the elastomer 200 such that they are spaced apart from each other at two sides of the test chamber 300 according to an embodiment, the exemplary embodiments are not limited thereto, and one main channel 400 may also be indented to the lower surface of the elastomer 200 such that the main channel 400 is arranged at one side of the test chamber 300. An inlet 401, through which the fluid or the cells described above are injected into the main channel 400 so as to be introduced into the test chamber 300, and an outlet 402, through which the fluid in the main channel 400 is discharged out of the main channel 400, may be respectively connected to two ends of the main channel 400.

The connection channel 500 is a flow path portion connecting the test chamber 300 and the main channel 400. That is, the connection channel 500 allows the fluid introduced into the main channel 400 to circulate inside the test chamber 300.

The connection channel 500 is arranged between the test chamber 300 and the main channel 400 so as to connect the test chamber 300 and the main channel 400 to each other. That is, while the connection channel 500 is arranged between the test chamber 300 and the main channel 400, the connection channel 500 is indented to the lower surface of the elastomer 200 at a predetermined height such that the connection channel 500 is connected to each of the test chamber 300 and the main channel 400.

A height of the connection channel 500 is lower than heights of the test chamber 300 and the main channel 400. Here, a height $h_1$ of the connection channel 500 and a height $h_2$ of the test chamber 300 are formed to have a height ratio of 1:10 to 1:100 before pressurizing of the pressure adjusting unit 600. If a height ratio of a height of the test chamber 300 to a height of the connection channel 500 is smaller than 10, space for cell culturing in the test chamber 300 may be small. In addition, if a height ratio of a height of the test chamber 300 to a height of the connection channel 500 is greater than 100, large elastic deformation is required.

The height $h_1$ of the connection channel 500 and a height $h_3$ of the main channel 400 are formed to be the same before and after pressurizing by the pressure adjusting unit 600 which will be described later.

Figure 4:
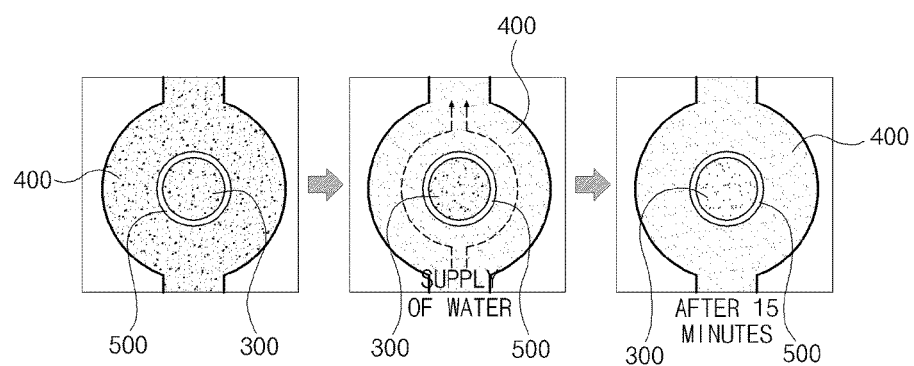
FIGS. 4 and 5 illustrate states of an environment of a micro cell culturing device controlled according to a fluid injected into the micro cell culturing device, according to an embodiment of the present invention.
Figure 5:
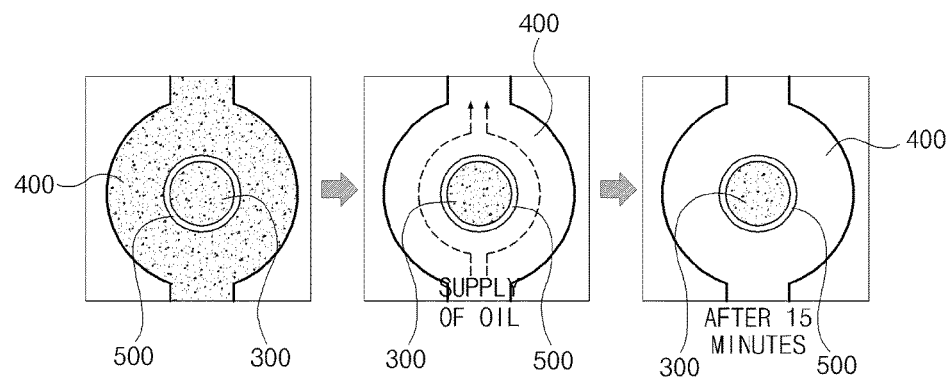
Figure 6:
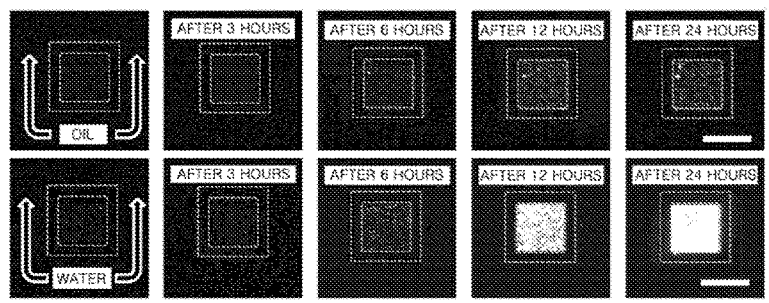
FIG. 6 illustrates a state of cell culturing according to FIGS. 4 and 5.

As the connection channel 500 is pressurized and compressed by using the pressure adjusting unit 600, which will be described later, the cells in the test chamber 300 are prevented from migrating to the main channel 400. That is, the height $h_3$ of the connection channel 500 is maintained at 50 nm to 500 nm due to compression of the elastomer 200 caused by the pressure adjusting unit 600, which will be described later, and only the fluid injected into the main channel 400 is diffused to be introduced into the test chamber 300, and the cells in the test chamber 300 may be maintained at their positions in the test chamber 300 regardless of a flow of the fluid introduced into the main channel 400. Here, if the fluid injected into the connection channel 500 is water, the water is diffused to be introduced into the main channel 400 through the connection channel 500. However, if the fluid injected into the connection channel 500 is oil, the oil is not diffused to be introduced into the main channel 400 through the connection channel 500. That is, when referring to FIGS. 4 and 5, in the case of FIG. 4, when water is injected as a fluid into the main channel 400, material transfer to the test chamber 300 is conducted via diffusion through the connection channel 500 so as to adjust a chemical environment of the test chamber 300, whereas in the case of FIG. 5, if oil is injected as a fluid into the main channel 400, material transfer to the test chamber 300 via diffusion through the connection channel 500 is not possible, and thus it is difficult to adjust a chemical environment of the test chamber 300. Thus, as shown in FIG. 6, if water and oil each including a nutritive substance of the same density are respectively injected into the main channel 400, a material transfer efficiency of water to cells in the test chamber 300 is increased so as to increase speed and efficiency of growth of the cells.

The pressure adjusting unit 600 pressurizes and compresses the elastomer 200. The pressure adjusting unit 600 may be, for example, a pressurizing device that is well-known and typically used. That is, a device that ejects gas onto an upper portion of the elastomer 200 to pressurize the elastomer 200 or a pressing unit well-known in the art may be selected and used as the pressure adjusting unit 600.

Figure 7:
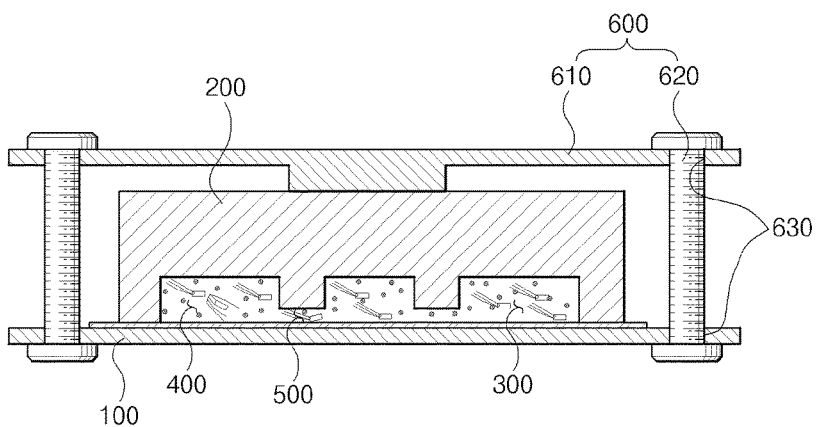
FIG. 7 is a cross-sectional view of a pressure adjusting unit illustrated in FIG. 2 according to another embodiment.

FIG. 7 illustrates another exemplary embodiment of the pressure adjusting unit 600, which may include a plate-shaped pressurizing plate 610 arranged on the elastomer 200 and an adjustment screw 620 having two ends in a length direction that are respectively screw-coupled to the pressurizing plate 610 and the substrate 100 so as to connect the pressurizing plate 610 and the substrate 100 to each other.

Here, a coupling hole 630 having a screw portion at a position corresponding to each of boundary portions of the pressurizing plate 610 and the substrate 100 is formed to pass through each of the boundary portions of the pressurizing plate 610 and the substrate 100. Also, while the adjustment screw 620 is screw-coupled to each of the coupling holes 630 of the pressurizing plate 610 and the substrate 100, the pressurizing plate 610 is slid upwards or downwards according to an axial rotational direction of the adjustment screw 620, thereby adjusting a compressive force that pressurizes the elastomer 200.

Figure 8:
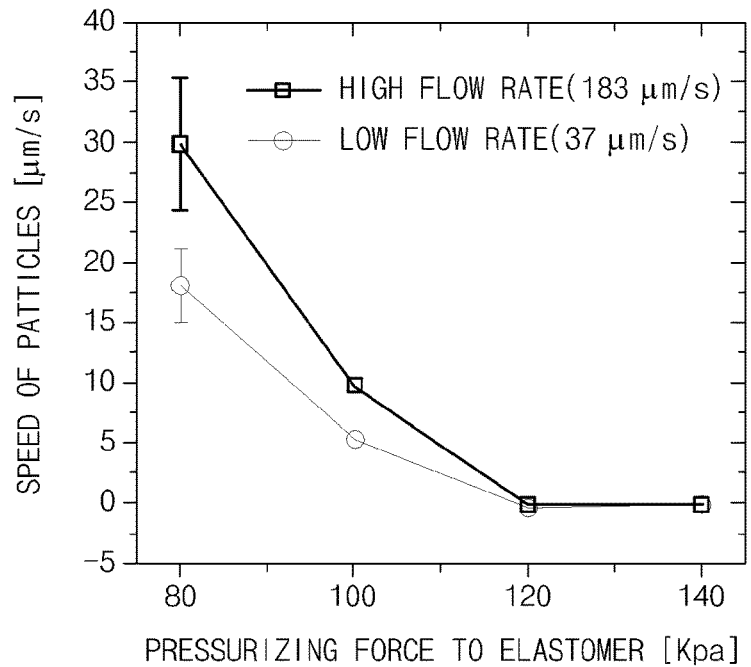
FIG. 8 is a graph showing displacement of cells in a test chamber according to a pressure of a pressure adjusting unit of a micro cell culturing device according to an embodiment of the present invention.

As described above, the pressure adjusting unit 600 pressurizes and compresses the elastomer 200, thereby preventing cells in the test chamber 300 from migrating to the main channel 400 through the connection channel 500. That is, the pressure adjusting unit 600 pressurizes and compresses the elastomer 200, and allows a height of the connection channel 500 to be smaller than a size of the cells in the test chamber 300. Referring to FIG. 8, as a pressurizing force of the pressure adjusting unit 600 is increased, even when a fluid is injected into the main channel 400, the cells in the test chamber 300 are hardly affected by a flow of the fluid. That is, a pressure of the pressure adjusting unit 600 affects the height of the connection channel 500, and as the pressure is increased, a diffusion speed of a fluid introduced into the main channel 400 into the test chamber 300 is reduced. Here, it is illustrated that, for example, if the pressure adjusting unit 600 pressurizes the elastomer 200 with a pressure of 120 KPa or greater, the cells in the test chamber 300 are not affected by a fluid flow of the main channel 400, but the exemplary embodiments are not limited thereto, and the pressure may also be adjusted according to a height and an area of each of the test chamber 300, the main channel 400, and the connection channel 500. Here, the pressure adjusting unit 600 pressurizes and compresses the elastomer 200, and maintains the connection channel 500 at a height of 50 nm to 500 nm at the same time, as described above.

Figure 9:
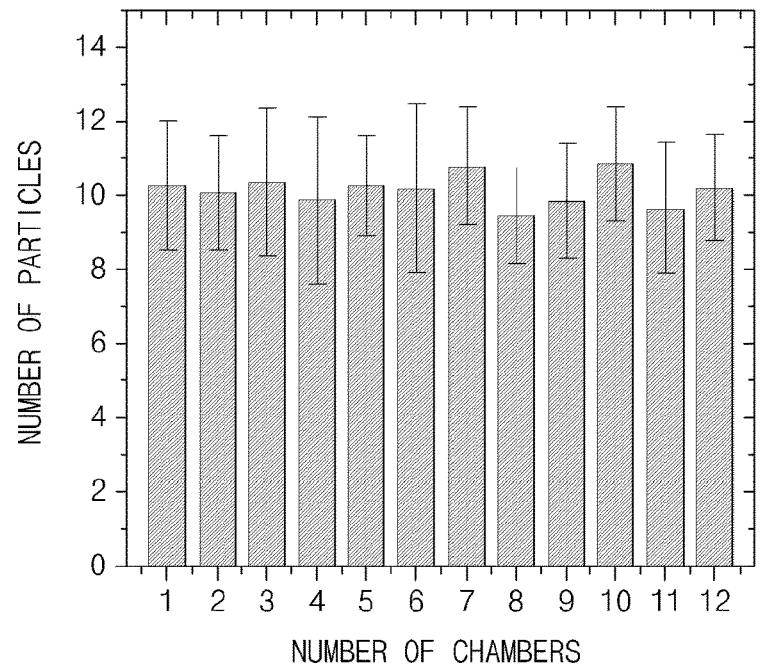
FIG. 9 is a graph showing quantification and partitioning of cells in a test chamber of a micro cell culturing device according to an embodiment of the present invention.

FIG. 9 shows a quantified number of cells in the test chamber 300 in the micro cell culturing device according to an exemplary embodiment, indicating that uniform application and partitioning of cells are possible.

As described above, according to the micro cell culturing device, the elastomer 200, into which the test chamber 300, the main channel 400, and the connection channel 500 are indented to a predetermined height, is seated and arranged on the substrate 100. While the connection channel 500 is formed at a lower height than the test chamber 300 and the main channel 400, the elastomer 200 is pressurized and compressed via the pressure adjusting unit 600. Accordingly, the connection channel 500 allows a fluid injected into the main channel 400, to diffuse into the test chamber 300, but prevents cells in the test chamber 300 from migrating to the main channel 400. Thus, culturing may be stably performed while the cells are maintained inside the test chamber 300.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A micro cell culturing device comprising:
   a substrate;
   an elastomer seated and arranged on an upper surface of the substrate;

a test chamber indented to a lower surface of the elastomer at a predetermined height, wherein the lower surface of the elastomer faces the upper surface of the substrate, and cells flow in the test chamber;

a main channel indented to the lower surface of the elastomer at a predetermined height, wherein the main channel is spaced apart from the test chamber, and cells flow in the main channel;

a connection channel indented to the lower surface of the elastomer at a predetermined height and arranged between the test chamber and the main channel to connect the test chamber and the main channel to each other; and a pressure adjusting unit configured to pressurize an entire surface of the elastomer so that pressure is applied to the test chamber, main channel, and the connection channel, wherein a height of the connection channel is lower than heights of the test chamber and the main channel before and after being pressurized by the pressure adjusting unit, and when the pressure adjusting unit pressurizes the elastomer, the connection channel is maintained at such a height that migration of the cells in the test chamber to the main channel is prevented, wherein the connection channel and the test chamber have a height ratio of 1:10 to 1:100 before being pressurized by the pressure adjusting unit.

2. The micro cell culturing device of claim 1, wherein the test chamber and the main channel have the same height.

3. The micro cell culturing device of claim 1, wherein the connection channel has a height of 50 nm to 500 nm due to the elastomer being pressurized by the pressure adjusting unit.

4. The micro cell culturing device of claim 1, wherein the elastomer is PDMS.

5. The micro cell culturing device of claim 1, wherein the pressure adjusting unit comprises:

a pressurizing plate having a plate shape and arranged on the elastomer; and an adjustment screw having two ends in a length direction that are respectively screw-coupled to the pressurizing plate and the substrate to connect the pressurizing plate and the substrate to each other.

\* \* \* \* \*